United States Patent
Bambal et al.

(10) Patent No.: US 6,756,209 B1
(45) Date of Patent: Jun. 29, 2004

(54) 7-ALKOXYCOUMARINS AS CYP2C9 SUBSTRATES AND ACTIVITY ASSAY

(75) Inventors: Ramesh B. Bambal, King of Prussia, PA (US); Richard Leonard Elliott, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/806,877
(22) PCT Filed: Oct. 4, 1999
(86) PCT No.: PCT/EP99/07416
§ 371 (c)(1),
(2), (4) Date: Jun. 11, 2001
(87) PCT Pub. No.: WO00/22159
PCT Pub. Date: Apr. 20, 2000

(30) Foreign Application Priority Data

Oct. 9, 1998 (GB) .............................. 9822140

(51) Int. Cl.$^7$ ........................... C12Q 1/34; C07D 3/102
(52) U.S. Cl. ........................................ 435/18; 549/283
(58) Field of Search .............................. 549/283; 435/18

(56) References Cited

U.S. PATENT DOCUMENTS 5,216,176 A * 6/1993 Heindel et al. ............. 549/280
6,207,404 B1 * 3/2001 Miller et al. ................ 549/283

OTHER PUBLICATIONS

C. L. Crespi, et al., "Microtiter Plate Assays" for Inhibition of Human, Drug–Metabolizing Cytochromes P450 Analytical Biochemistry, U.S. Academica Press, San Diego, CA, vol. 248, No. 248, pp. 184–190.

Mace, et al., "Development of CYP450–Expressing Human Bronchial Epithelial Cell Lines for In Vitro Pharmacotoxicologic Applications", In–Vitro Toxicology, vol. 10, No. 1, (1997), 85–92.

C. Aubert et al., "Methode Generale d'Acces aux Trifluoromethylcetones. Lere Partie Alkylation Directe du trifluoroacetylacetate d'Ethyle" Journal of Fluorine Chemistry, vol. 44, 1989, pp. 361–376.

S. C. Laskowski and R. O. Clinton, "Coumarins. II. Derivatives of Coumarin–3– and –4–Acetic Acids", Journal of the American Chemical Society, vol. 72, Sep. 1950, pp. 3987–3991.

M. Masai. et al., Synthesis. Fourescence and Photostabilities of 3–(Perfluoroalkyl)coumarin) Chemische Berichte, vol., 125, 1992, pp. 467–471.

R. E. Pastor, et al., "Etude en Resonance Magnetique, Nucleaire du 13C des F–methyl–4coumarines" Canadian Journal of Chemistry, vol. 65, 1987, pp. 1356–1360.

* cited by examiner

Primary Examiner—Sandra E. Saucier
(74) Attorney, Agent, or Firm—Nora Stein-Fernandez; Theodore R. Furman; Charles M. Kinzig

(57) ABSTRACT

Coumarin derivatives as substrates for cytochrome P450 enzyme.

8 Claims, 1 Drawing Sheet

7-ALKOXYCOUMARINS AS CYP2C9 SUBSTRATES AND ACTIVITY ASSAY

Figure 1:
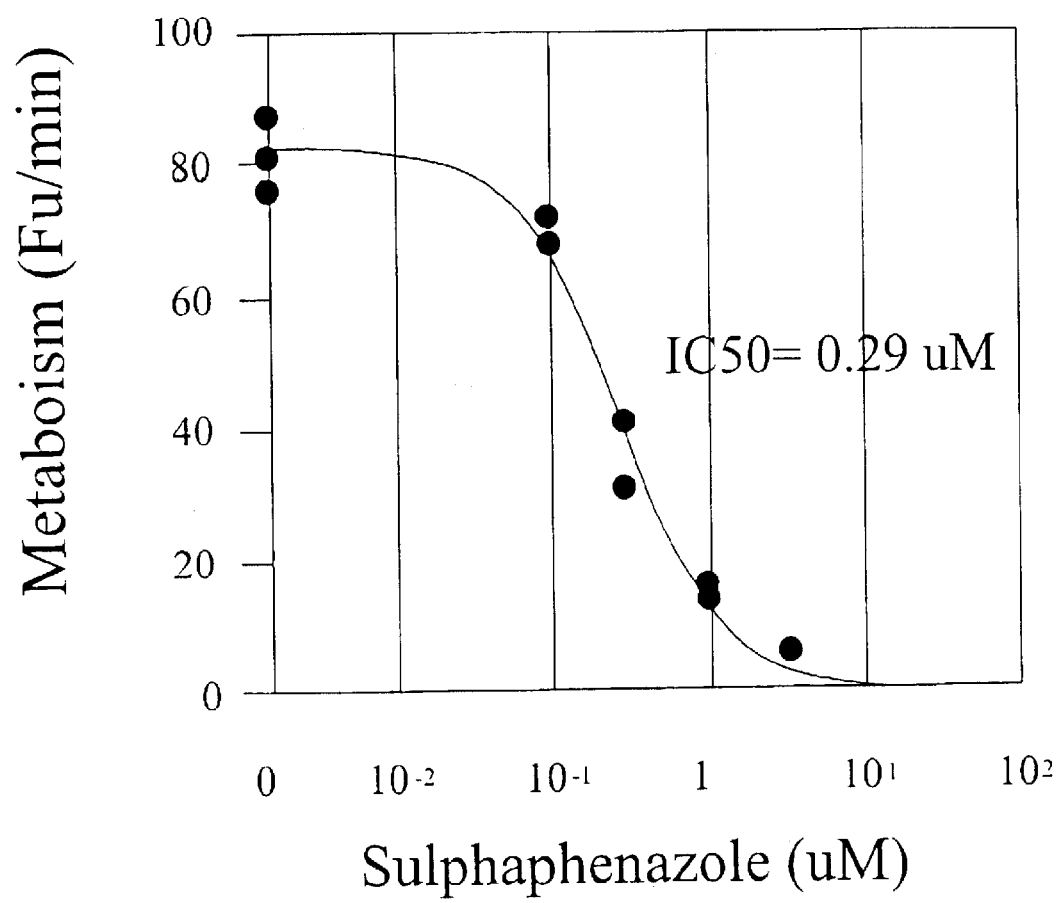

This invention relates to compounds, processes for preparing them and their use as enzyme substrates.

The majority of metabolism based drug interactions are a result of inhibition of cytochrome P450 enzymes. Drug interactions involving individual P450 enzymes can be predicted using in vitro methods. Typical in vitro P450 enzyme assays involve incubation of an appropriate substrate with a source of enzyme. Traditionally time consuming chromatographic methods have been used for metabolite detection in these incubations. More recently the availability of fluorimetric plate readers has facilitated tne higher throughput of enzyme assays in general. Adapting P450 assay to fluorescent plate reader technology requires the identification of substrates with appropriate fluorescent products for individual enzymes. Among the xenobiotic-metabolising cytochromes P450, CYP2C9 is one of those commonly responsible for the metabolism of drugs.

3-Cyano-7-ethoxycoumarin has been described for high throughput CYP2C9 inhibition screening (Crespi et al. *Anal. Biochem.*, 1997: 248, 188–190). However, the rate of 3-cyano-7-ethoxycoumarin metabolism by CYP2C9 is low and the extent of 3-cyano-7-ethoxycoumarin O-dealkylase inhibition does not always correlate well with a solid-phase extraction assay for CYP2C9, thus 3-cyano-7-ethoxycoumarin is not suitable for high throughput screening.

Certain compounds have now been identified which are improved substrates for CYP2C9 and which are of use for configuring high throughput inhibition screening assays.

According to the present invention there is provided an assay for testing for inhibitors of the enzyme CYP2C9 which comprises contacting the enzyme and a compound of formula (I):

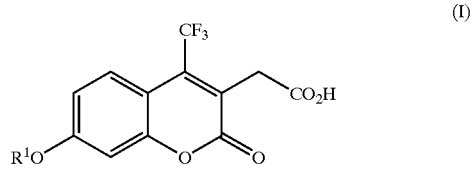

(I)

wherein $R^1$ represents $C_{1-2}$alkyl, with a test compound and measuring inhibition of O-dealkylation of the compound of formula (I) by the enzyme.

In a preferred aspect of the invention $R^1$ is methyl.

Generally, the rate of O-dealkylation of the compound of formula (I) in the absence of test compound will be known, as will the extent of O-dealkylation at given time points. The assay may test for inhibition of O-dealkylation continuously or at specified time points.

O-Dealkylation of the compound of formula (I) following incubation with CYP2C9 gives a readily quantifiable fluorescent product of formula (II):

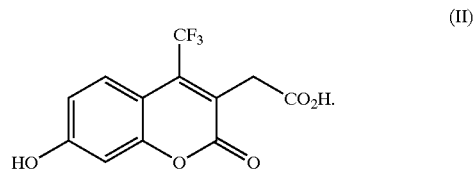

(II)

which can be scanned with suitable excitation and emission wavelengths, for example an excitation wavelength of 410 nm and an emission wavelength of 510 nm.

The assay may be carried out either in solution or utilising a solid support. When the assay is carried out in solution suitable solvents include methanol, acetonitrile and DMSO.

The test compound may be pre-incubated with enzyme prior to the addition of the substrate, or alternatively the substrate may be added simultaneously. Final concentrations of enzyme and substrate are calculated so as to achieve a suitable rate of processing for carrying out the assay. If desired, the reaction may be stopped, for example by addition of acid or solvent. The fluorescent product of formula (II) may be analysed using any conventional system of fluorescence detection, for example a multi-well plate/fluorescent plate reader.

The compounds of formula (I) and (II) are novel and as such also form part of the invention.

The compounds of formula (I) and (II) may be prepared by conventional methods, for example as shown in Scheme 1:

Scheme 1

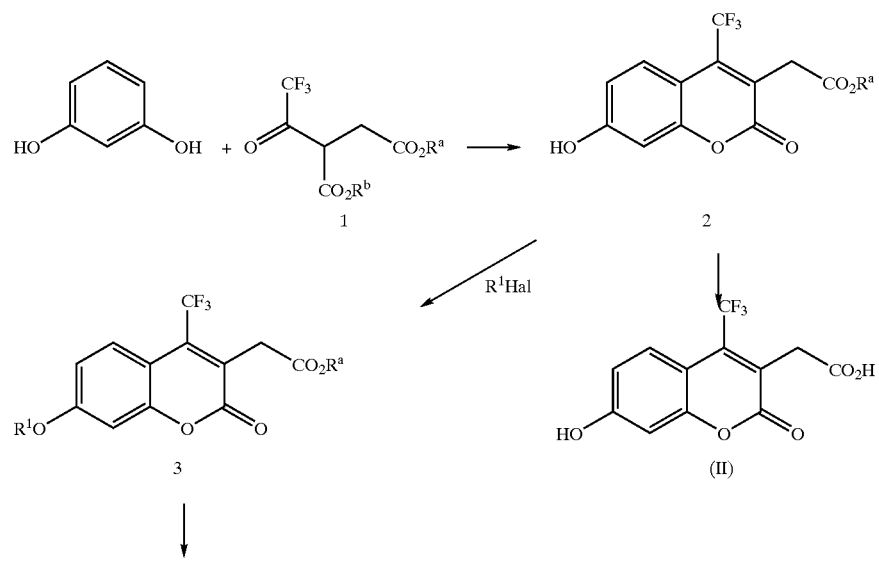

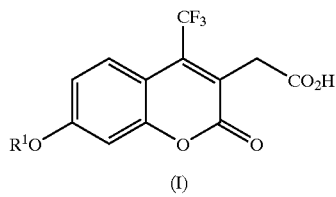

(I)

$R^1$, $R^a$ and $R^b$ are independently methyl or ethyl

Thus according to a further aspect of the invention there is provided a process for the production of a compound of formula (I) or (II) which comprises:
a) reaction of resorcinol and a dialkyl trifluoroacetosuccinate wherein the alkyl groups are independently selected from $C_{1-2}$ alkyl, in the presence of polphosphoric acid;
b) for compounds of formula (I) reaction of the resulting 7-hydroxycoumarin with a compound of formula $R^1$Hal, wherein $R^1$ is $C_{1-2}$ alkyl and Hal is halogen e.g. iodine or bromine; and
c) ester hydrolysis to give the acid of formula (I) or (II).

The reaction of resorcinol with a dialkyl trifluoroacetosuccinate in the presence of polyphosphoric acid may suitably be performed at a temperature of about 15–30° C.

Typical reaction conditions for the alkylation of a 7-hydroxycoumarin with an alkylhalide are well known to those skilled in the art and include a solvent such as acetone at reflux in the presence of a base such as potassium carbonate.

Typical reaction conditions for ester hydrolysis are well known to those skilled in the art and include dilute hydrochloric acid in methanol or ethanol at reflux Dialkyl trifluoroacetosuccinates of formula I may be prepared from the corresponding alkyl bromoacetate and alkyl trifloroacetoacetate according to the route described in C. Aubert et al. *J. Fluorine Chem.* 1989, 44,361. Suitable alkyl bromoacetates and alkyl trifluoroacetoacetates are commercially available.

Since the inhibition of cytochrome P450 enzymes is often the mechanism for drug/drug interactions, the assay according to the invention is particularly useful for identifying compounds which may give rise to adverse drug/drug interactions. The assay can therefore be used in combination with the chemical modification of test compounds to increase a test compound's potential for use as a pharmaceutical.

Thus according to further aspects of the invention there are provided a method for reducing the CYP2C9 enzyme inhibitory activity of a compound, comprising the steps of identifying the compound as an inhibitor of CYP2C9 in the assay described above; and thereafter producing a chemically modified version of the test compound in which the functionality suspected to be responsible for CYP2C9 inhibition is eliminated or changed; and novel compounds produced according to this method.

The chemical modification of test compounds according to this method can be performed using techniques well known to those skilled in the art.

The novel compounds produced according to this aspect of the invention may find application as pharmaceuticals. A compound produced according to this method will be readily identifiable as novel by performinq routine literature and database searches. The pharmaceutical activity of such compounds can be readily ascertained using conventional biological screening methods known to those skilled in the art.

All publications including, but not limited to patents and patent applications, cited in this specification are herein incorporated by reference as if each individual publication were specifically and individually indicated to be incorporated by reference herein as though fully set forth.

The invention is illustrated by the following examples.

EXAMPLE

Preparation of 7-methoxy-4-trifluoromethylcoumarin-3-acetic acid.

a) 7-Hydroxy-4-trifluoromethyl coumarin-3-acetic acid ethyl ester [2, $R^a$=Et]

Polyphosphoric acid (45 g) was added to a mixture of resorcinol (4.06 g) and diethyl trifluoroacetosuccinate (9.96 g) (Aubert C. Begue, J. P.; Charpentier-Morize, M.; Nee, G.; Langlois, B. *J. Fluorine Chem.* 1989, 44,361). The mixture was stirred at room temperature for 24 h. Crushed ice was added and the mixture extracted with dichloromethane. The organic phase was washed with water then dried ($MgSO_4$) and evaporated. The residue was purified by chromatography on silica gel (eluent 2% methanol in dichloromethane) to give the title compound (1.24 g) m.p. 112.5–114.0° C. $\delta_H$($CDCl_3$) 1.30 (t,3H), 3.96 (m,2H), 4.24 (q.2H), 6.66 (d,J=2.5 Hz 1H), 6.75 (dd.J=9.0, 2.5 Hz, 1H), 7.55 (m,1H); mass spectrum m/z 317 ($MH^+$).

b) 7-Methoxy-4-trifluoromethyl coumarin-3-acetic acid ethyl ester [3,$R^1$=Me,$R^a$=Et]

Methyl iodide (0.41 ml) was added to a mixture of 2(0.7 g) potassium carbnonate (0.46 g) and acetone (15 ml). The mixture was heated under reflux for 5 h. After cooling the solvent was evaporated and the residue was partitioned between dichloromethane and water. The organic phase was washed with water and then dried ($MgSO_4$) and evaporated. The residue was purified by chromatopgraphy on silica gel (eluent 0.5% methanol in dichloromethane) to give the title compound (0.62 g) $\delta_H$($CDCl_3$) 1.26 (t, 3H), 3.90 (s, 3H), 3.94 (m, 2H), 4.19 (q, 2H), 6.86 (d,J=2.6,Hz, 1H), 6.91 (dd,J=9.2, 2.6 Hz, 1H), 7.70 (m,1H); mass spectrum m/z 331 ($MH^-$).

c) 7-Methoxy-4-trifluoromethyl coumarin-3- acetic acid [(I), $R^1$=Me]

A mixture of 3 (0.615 g), ethanol (5 ml) and dilute hydrochloric acid (3M, 100 ml) was heated under reflux. After 6 h the mixture was cooled and the solid collected by filtration. The dried solid was crystallised from diethyl ether/hexane to give the title compound (0.475 g) m.p. 198.5–200° C. Found: C. 51.60: H, 2.82 $C_{13}H_9F_3O_5$ requires C,51.67, H, 3.00%; $\delta_H$($CDCl_3$) 3.90 (s, 3H, 3.94 (m, 2H), 6.87 (d,j=2.6 Hz, 1H), 6.92 (ddJ=9.2, 2.6 Hz, 1H), 7.70 (m, 1H), mass spectrum m/z 325 ($M+Na^{30}$), 303 ($MH^+$), 285 ($M-OH^-$).

Assay methodology
Materials:
  6.25 mM 7-Methoxy-4-trifluoromethylcoumarin-3-acetic acid (i.e. 1.88 mg/mL in DMSO)
  2% (w/v) NaHCO$_3$—stored at approx. 4° C.
  50 mM potassium phosphate buffer, pH 7.4
  Freshly prepared ofactor solution —approx. the following per mL of 2% (w/v) NaHCO$_3$
  1.7 mg NADP, monosodium salt
  7.8 mg glucose-6-phosate, monosodium salt
  6 Units glucose-6-phosphate dehydrogenase, Type VII from Bakers Yeast Method:
1) Mix 1 μL 6.25 mM 7-methoxy-4-trifluoromethylcoumarin-3-acetic acid, 10 μL (100 μg) CYP2C9 microsomal protein and 209 μL buffer per incubate (giving (25 μM 7-methoxy-4-trifluoromethylcoumarin-3-acetic and 400 μg/mL protein final concentration).

2) To each well of a 96-well plate add 220μL of incubation mix and 5 μL of test compound in methanol, (or 5 μL of appropriate solvent for control wells—methanol, acetonitrile or DMSO may be used).

3) Pre-incubate the multi-well plate in the plate reader at 37° C., for 5 minutes. Pre-warm the cofactor solution at 37° C. for 5 minutes.

4) Add 25μL cofactor solution to each well and scan with an excitation wvelength of 410 nm and an emission wavelength of 510 nm with a gain of 80. Scan for 10 cycles at 1 minute intervals.

Results

Confirmation of 7-methoxy-4-trifluoromethylcoumarin-3-acetic acid as a CYP2C9 substrate was achieved using sulphaphenazole, a doagnostic CYP2C9 inhibitor (Back et al. *British Journal of Clinical Pharmacology*, 1988, 26, 23–29). With sulphaphenazole, 7-methoxy-4-trifluoromethylcoumarin-3-acetic acid was inhibited with an IC$_{50}$ of 0.29 μM (FIG. 1), an inhibition value typical of other, well characterised, CYP2C9 substrates.

What is claimed is:

1. An assay for testing for inhibitors of the enzyme CYP2C9 which comprises contacting the enzyme and a compound of formula (I):

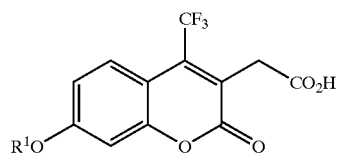

(I)

wherein R$^1$ represents C$_{1-2}$alkyl, with a test compound and measuring inhibition of O-dealkylation of the compound of formula (I) by the enzyme.

2. The assay according to claim 1 wherein R$^1$ is methyl.

3. The assay according to claim 1 wherein inhibition of O-dealkylation of the compound of formula (I) by the enzyme is measured by quantifying the compound of formula (II):

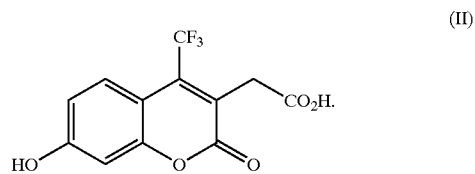

(II)

4. The assay according to claim 3 wherein the compound of formula (II) is quantified by fluorescence detection.

5. The assay according to claim 4 wherein the compound of formula (II) is quantified by scanning at excitation wavelength of 410 nm and an emission wavelength of 510 nm.

6. A compound of formula (I) as defined in claim 1.

7. A process for the production of a compound of formula (I) as defined in claim 6 which comprises:
  a) reacting resorcinol and a dialkyl trifluoroacetosuccinate wherein the alkyl groups are independently selected from C$_{1-2}$ alkyl, in the presence of polyphosphoric acid;
  b) reacting the resulting 7-hydroxycoumarin with a compound of formula R$^1$Hal, wherein R$^1$ is C$_{1-2}$ alkyl and Hal is halogen; and
  c) hydrolyzing to give the acid of formula (I).

8. A process for the production of a compound of formula (I) as defined in claim 6 which comprises:
  a) reacting resorcinol and a dialkyl trifluoroacetosuccinate wherein the alkyl groups are independently selected from C$_{1-2}$ alkyl, in the presence of polyphosphoric acid;
  b) reacting the resulting 7-hydroxycoumarin with a compound of formula R$^1$Hal, wherein R$^1$ is C$_{1-2}$ alkyl and Hal is a halogen selected from iodine or bromine; and
  c) hydrolyzing to give the acid of formula (I).

* * * * *